(12) United States Patent
Prins

(10) Patent No.: US 7,432,714 B2
(45) Date of Patent: Oct. 7, 2008

(54) METHOD AND DEVICE FOR ON-CHIP MAGNETIC RESONANCE SPECTROSCOPY

(75) Inventor: Menno Willem Jose Prins, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/587,447

(22) PCT Filed: Jan. 14, 2005

(86) PCT No.: PCT/IB2005/050158

§ 371 (c)(1), (2), (4) Date: Jul. 25, 2006

(87) PCT Pub. No.: WO2005/073695

PCT Pub. Date: Aug. 11, 2005

(65) Prior Publication Data

US 2007/0159175 A1    Jul. 12, 2007

(30) Foreign Application Priority Data

Jan. 26, 2004    (EP)    ................... 04100267

(51) Int. Cl.
*G01V 3/00*   (2006.01)
(52) U.S. Cl. .................................................. 324/322
(58) Field of Classification Search .......... 324/300–322
See application file for complete search history.

(56) References Cited

U.S. PATENT DOCUMENTS 5,585,722 A * 12/1996 Hosoki et al. ............... 324/318
6,194,900 B1 * 2/2001 Freeman et al. ............. 324/321
6,294,914 B1 * 9/2001 Fiat ............................. 324/312
6,429,640 B1 * 8/2002 Daughton et al. ........ 324/117 R
6,710,879 B1 * 3/2004 Hansen et al. .............. 356/436
6,731,100 B1 * 5/2004 Hansen et al. ............. 324/71.4
6,906,793 B2 * 6/2005 Bamji et al. .............. 356/141.1
7,048,890 B2 * 5/2006 Coehoorn et al. ........ 422/82.02

FOREIGN PATENT DOCUMENTS

JP    03260906 A  * 11/1991

OTHER PUBLICATIONS

Stewart Bushong, "Magnetic Resonance Imaging Physical and Biological principles", second edition; pp. 28-30 and 160-163.*
Boero G et al: "Fully Integrated Probe for Proton Nuclear Magnetic Resonance Magnetometry"; Review of Scientific Instruments AIP USA; vol. 72 No. 6; 2001; pp. 2764-2768.
Trumbull J D et al: "Integrating Microfabricated Fluidic Systems and NMR Spectroscopy"; IEEE Transactions on Biomedical Engineering, IEEE Inc. New York, US vol. 47, No. 1; Jan. 2000; pp. 3-7.

* cited by examiner

Primary Examiner—Brij B. Shrivastav
Assistant Examiner—Dixomara Vargas

(57) ABSTRACT

A method and a device for on-chip magnetic resonance spectroscopy is proposed. On-chip magnetic resonance spectroscopy may be applied to non-magnetic as well as magnetic materials which may be solids, liquids, or gases. The method of the present invention is suitable for miniaturized materials analysis such as, for example, micro-fluidics. In an example embodiment, the method relies on the combination of highly efficient spin excitation near on-chip current wires with very sensitive on-chip magnetic sensors. The method and device also allows one to separately detect different types of magnetic particles or molecules.

25 Claims, 3 Drawing Sheets

METHOD AND DEVICE FOR ON-CHIP MAGNETIC RESONANCE SPECTROSCOPY

The present invention relates to a method and device for on-chip magnetic resonance spectroscopy. The method may be applied to non-magnetic as well as to magnetic materials and to solids, liquids and gases and may be suitable for miniaturised materials analysis, such as for example microfluidics. The method may also be applied in molecular diagnostics, e.g. using separately detectable labels.

Magnetic resonance spectroscopy is a general method to analyse materials which is widely applicable and offers a direct and detailed insight at the atomic and nuclear level of materials. Magnetic resonance is based on the orientation and precession of magnetic spins inside a sample that has to be analysed. Depending on the origin of the magnetic spin, two major groups of magnetic resonance techniques can be distinguished, i.e. nuclear magnetic resonance (NMR) and electron spin resonance (ESR), often also called electron paramagnetic resonance (EPR).

Nuclear Magnetic Resonance is a branch of spectroscopy in which electromagnetic radiation (usually of radiowave frequency) is absorbed by molecules possessing nuclei with non-zero spins, i.e. nuclear spin quantum number I>0. On the other hand, in electron paramagnetic resonance or electron spin resonance electromagnetic radiation (usually of microwave frequency) is absorbed by molecules, ions or atoms possessing electrons with unpaired spins, i.e. electronic spin quantum number S>0.

The orientation of the spin can either be parallel to the external magnetic field or anti-parallel to the external magnetic field. This creates two different energy states depending on the spin orientation. In the case of a coupled system of electron spins, different energy states also are created depending on the electron spin configuration of the coupled system. The population of spins or of coupled systems of spins of the samples than has an equilibrium distribution wherein, depending on the temperature and the magnetic fields, a certain amount of spins or coupled systems of spins then is in a first energy state whereas a certain amount of spins or coupled systems of spins is in a second energy state.

For magnetic resonance spectroscopy purposes the nuclear (NMR) or respectively electron (EPR) spin quantum number must be equal to ½ n, where n is an integer 1,2,3 . . . etc. Materials for which the spin quantum number equals zero do not exhibit magnetic resonance phenomena. If, for example, the spin quantum number equals ½ (n=1 and thus I=½ or S=½), there are only two possible spin states, i.e. $m_I$ (NMR) resp. $m_s$ (EPR)=±½. In the absence of a magnetic field these two states are degenerate. If a magnetic field is applied, the levels split apart with an energy separation $\Delta E$ proportional to the magnetic field strength $B_0$ (FIG. 1). This splitting is known as the Zeeman effect. Even in a large magnetic field the levels are relatively close together. The energetically preferred orientation of the spin has a magnetic moment aligned parallel with the applied field (spin +½) and is often given the notation α, whereas the higher energy anti-parallel orientation (spin −1½) is referred to as The energy difference between both orientations in case of NMR (FIG. 1) is given by Eq. 1:

$$\Delta E = h\nu = -\frac{h\gamma B_0}{2\pi} = -\hbar\gamma B_0 \quad (\text{Eq. 1})$$

with h the Planck constant, v the resonance frequency, $B_0$ the field strength of the external magnetic field and γ the magnetogyric ratio.

In case of EPR (FIG. 2) the difference between both orientations is:

$$\Delta E = h\nu = g\mu_B B_o \quad (\text{Eq.2})$$

with g the Zeeman splitting factor, $\mu_B$ the Bohr magneton and $B_0$ the field strength of the external magnetic field.

The magnetogyric ratio as well as the Zeeman splitting factor are constants that are typical for the studied material. These will allow to use magnetic resonance as a characterisation technique. NMR and EPR characterisation techniques both are based on the same principle. By irradiating material in a homogeneous magnetic field with electromagnetic radiation of the correct energy, i.e. with a correct frequency, a nucleus (NMR) or an electron (EPR) with a low energy orientation can be induced to "jump" to a higher energy orientation. The absorption of energy during this transition forms the basis of the magnetic resonance method and can be detected, amplified and recorded as a spectral line, the so-called resonance signal. In continuous wave experiments two possible ways of detection are used frequently. In a first way of detection, the material to be studied is brought into a constant magnetic field, leading to a fixed energy difference between the different energy states corresponding with the different spin states and the material is irradiated with electromagnetic radiation of varying frequency. In this case, if the photon energy of the electromagnetic radiation corresponds with the energy difference between different energy states, a resonant absorption will occur and an absorption peak will be monitored in the spectrum. The resonance frequency, also called Larmor frequency, then allows characterisation of the material. In another way of detection, the photon energy of the electromagnetic radiation used for irradiating the material is kept constant, but the magnetic field is varied and an absorption peak is monitored if the energy difference between the energy states corresponding with different spin states, which consequently is also changed, matches the photon energy. Thus in the latter method, the magnetic field strength is varied continuously. In this way a NMR or EPR spectrum with one or more peaks, depending on the material that is analysed, can be generated. The frequencies at which the peaks appear reflect the Zeeman splitting factor or the magnetogyric factor and thus are typical for a certain material. Hence, by using NMR or EPR, samples of unknown composition may be analysed. Examples of the use of NMR are described in "Nuclear Magnetic Resonance in Solid Polymers", McBrierty and Packer, Cambridge Solid State Science Series, 1993.

Table 1 illustrates the difference in required radiation frequency between NMR and EPR. It may be seen that for a magnetic field strength of about 1T, NMR is usually observed at lower radio frequencies (MHz) while ESR usually requires microwave-frequency radiation (GHz).

TABLE 1

| Technique | Radiation frequency | |
|---|---|---|
| NMR | $\sim 60 \times 10^6$ to $600 \times 10^6$ Hz | Probes nucleus' magnetic field |
| ESR | $\sim 1 \times 10^9$ to $30 \times 10^9$ Hz | Probes electron's magnetic field |

When magnetic resonance is applied to materials with exchange-coupled spins, a coherent dynamics of spins is generated. This is called ferromagnetic resonance (FMR) or superparamagnetic resonance (SPR). A difference between superparamagnetic and ferromagnetic particles is given by the ratio $K.V/k_BT$, with K the magnetic anisotropy (e.g. shape anisotropy or crystal anisotropy) and V the volume of the magnetic particle. A high magnetic anisotropy leads to particles with ferromagnetism, a low anisotropy leads to superparamagnetism. In an FMR or SPR experiment, the field experienced by the coupled spins is given by the sum of the external field, the anisotropy fields and the demagnetising field. In the case of superparamagnetism, the second and third contributions are modified by superparamagnetic fluctuations.

Besides continuous wave situations, magnetic resonance techniques also can be performed by measuring a change in magnetisation for a material influenced by a permanent magnetic field and a perturbing pulsed electromagnetic field. Assuming that the first orienting field is applied along a z'-axis, if the pulsed electromagnetic field is applied under the proper conditions in terms of frequency, magnitude and duration, and having a field component perpendicular to the z'-axis, the energy is efficiently transferred to the material, leading to a change in the net magnetic moment, now having a component perpendicular to the z'-axis. The time-dependent orientation and relaxation of this magnetic moment or of one of its component, e.g. the magnetic moment in the x'-direction or the magnetic moment in the z'-direction, then can be measured. Again, varying the permanent magnetic field or the frequency of the electromagnetic field offers two methods for measuring.

In the prior art, the resonance is generally excited and detected with one or more field coils. For example in double coil NMR, exciting and detecting resonance occurs with two different coils.

When only very small sample volumes are available or when one is interested in materials properties on a local scale, it is important to reduce the size of the magnetic-resonance detection system. A disadvantage of the prior art systems for measuring magnetic resonance spectroscopy is that the signal-to-noise ratio rapidly decreases with miniaturisation of the systems. Therefore, the large systems used in the prior art, rapidly loose sensitivity when downscaled to an on-chip design size.

It is an object of the present invention to provide a method and device for on-chip magnetic resonance measurements such as for example magnetic resonance spectroscopy (e.g. NMR, EPR, ESR, FMR, SPR) which has good sensitivity and can be scaled down efficiently.

The above objective is accomplished by a method and device according to the present invention.

In an example embodiment, the present invention provides a device for on-chip resonance measurements for use with a first orienting magnetic field. The device comprises a chip. The chip comprises an on chip means for creating a second electromagnetic field to excite precession of oriented spin magnetic moments in a sample to be analyzed. There is at least one magnetic sensor for on-chip detection of a magnetic precession of the spin magnetic moments about the first orienting magnetic field in the sample to be analysed.

The spin magnetic moments may for example be nuclear spin magnetic moments, electron spin magnetic moments or coupled-spin magnetic moments. The magnetic resonance measurements may for example be magnetic resonance spectroscopy such as NMR, EPR, ESR, FMR, SPR.

In specific embodiments, the magnetic sensor may be for example a magneto-resistance sensor, such as for example a GMR, a TMR or an AMR sensor. The magneto-resistance sensor may have an elongate strip geometry. Furthermore, also other sensors may be used with the invention, such as for example Hall sensors, magneto-impedance sensors or magneto-striction sensors.

In one embodiment of the present invention, the chip is lying in a plane and the on-chip means for creating a second electromagnetic field and the magnetic sensor may be positioned adjacent to each other in the plane of the chip. Furthermore, the means for creating a second magnetic field and the magnetic sensor may be in a left-right position to each other but also in other respective positions such as e.g. at different depths in the substrate, above/below each other, etc.

In another embodiment, the chip is lying in a plane and the means for creating a second electromagnetic field may comprise a conductor adjacent the magnetic sensor. In still another embodiment, the chip is lying in a plane and the means for creating a second electromagnetic field may comprise two conductors, each of the conductors being positioned adjacent one of two opposite sides of the magnetic sensor at a same position with respect to the plane of the chip.

In a specific embodiment of the invention, the chip may comprise two means for creating a second magnetic field and a sensor. In this embodiment, one means for creating a second magnetic field may be positioned above the sensor and the other means for creating a second magnetic field may be positioned below the sensor.

The device according to the invention may furthermore comprise a first orienting magnetic field generator external to the chip. The first orienting magnetic field generator may for example be a permanent magnet or an electromagnet. Furthermore, the first orienting magnetic field generator may comprise a means to vary a magnetic field strength.

In the device according to the present invention, the chip may furthermore comprise an on-chip first orienting magnetic field generator. The chip may have two major surfaces opposite to each other. In an embodiment, the means for creating a second electromagnetic field and the magnetic sensor may be located on a first major surface and the on-chip first orienting magnetic field generator may be positioned on the second major surface.

In another example embodiment, the present invention furthermore provides a method for performing on-chip magnetic resonance measurements. The method comprise orienting spin magnetic moments inside a sample in a first orienting field. Inside the sample to be analyzed, the precession of the spin magnetic moments are excited. With a magnetic sensor, the spin magnetic moments precession is detected on-chip.

The magnetic resonance measurements may, for example, be magnetic resonance spectroscopy such as NMR, EPR, ESR, FMR, and SPR.

In an embodiment of the invention, on-chip detecting of spin magnetic moments precession may be performed by means of a magneto-resistance sensor.

Generating the spin magnetic moments in the first magnetic field may in one embodiment be performed by the first magnetic field being generated external to the chip. In another embodiment, generating the first orienting magnetic field may be performed by a magnetic field generator integral with the chip.

In an embodiment of the present invention, exciting precession of spins inside a sample to be analysed may be performed by generating a second magnetic field. In still another embodiment, exciting precession of spins inside a sample to be analysed may be performed by sweeping the second magnetic field over a frequency and/or amplitude range.

The method according to the present invention may furthermore comprise sweeping the first orienting magnetic field over a frequency and/or amplitude range.

The sample to be analysed with the method and device according to the present invention may comprise different types of magnetic particles or molecules. On-chip detecting of spin magnetic moments precession by means of a magnetic sensor may then comprise detecting separate signals originating from different types of magnetic particles or molecules.

The method and device according to the present invention may be used for biological sample analysis or chemical sample analysis.

The method and device of the present invention scales favourably with miniaturisation and is suited for integration in, for example, silicon technology. Furthermore, the method of the present invention is suitable for miniaturised material analysis such as for example in microfluidics.

A further advantage of the method of the present invention is that it is suitable for analysing non-magnetic as well as magnetic materials. Furthermore, the method may be applied for analysing solids, liquids or gases. One strength of the method of the present invention lies in the combination of a highly efficient magnetic excitation near on-chip conductors with sensitive on-chip magnetic sensors.

A further advantage of the method of the present invention is that it allows magnetic diagnostics having a low background signal and the possibility to actuate labels for stringency and target extraction.

A further advantage of the method of the present invention is that it allows label multiplexing.

Applications that can benefit from improved magnetic-resonance technologies as provided by the present invention are chemical and biochemical testing. An example is biomolecular diagnostics, the diagnostics of biological molecules and biological materials (e.g. proteins, cells, cell fragments, tissue, skin, blood, etc.) for biomedical and biotechnology applications. Such diagnostically testing generally involves a sequence of process steps, the so-called assay. Examples of assay steps are sample taking, filtering, sample dilution, dissolving additional reagents, breaking of cells, material extraction, concentration, amplification, capture and/or hybridisation (e.g. incubation with labels and binding to a surface), application of stringency (e.g. washing), and detection of labels. Key performance parameters are the sensitivity and specificity of the assay, as well as the speed, ease-of-use, reliability, reproducibility, integration and costs of the test. Biochemical assays will be able to benefit from improvements in magnetic resonance in a very general way when labels with specific magnetic resonance characteristics can be detected. Labels can also be called probes or reporters. A further application that can benefit is (bio)chemical testing that simultaneously uses different types of labels in an assay, e.g. to allow the use of concurrent controls, for comparative binding/hybridisation assays, and to reduce non-specific cross-signals in a multiplexed assay. The use of separately detectable labels can be referred to as 'label multiplexing'. Label multiplexing has not been demonstrated yet in magnetic diagnostics, as it requires separable signals and a high signal to noise ratio.

These and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
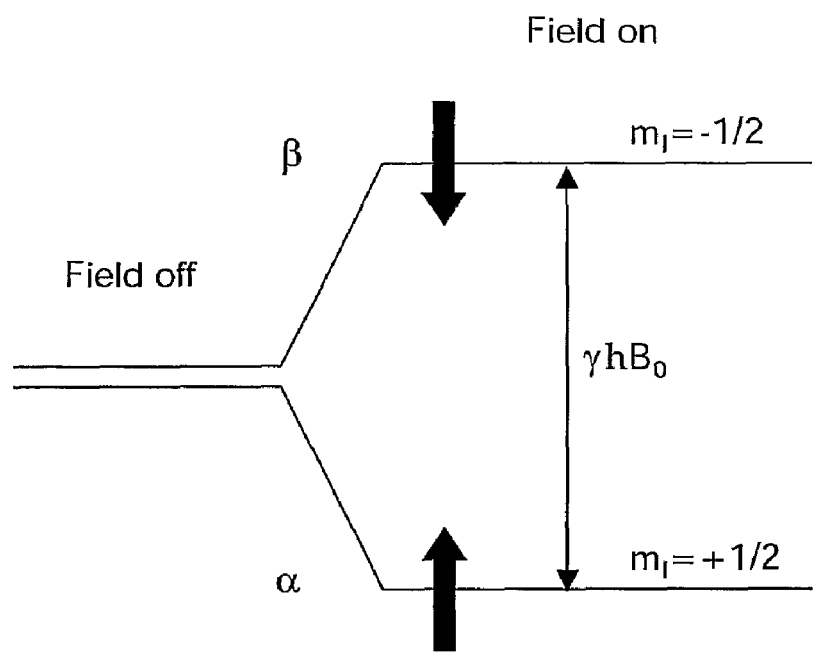
FIG. 1 is an illustration of the Zeeman effect in case of NMR.
Figure 2:
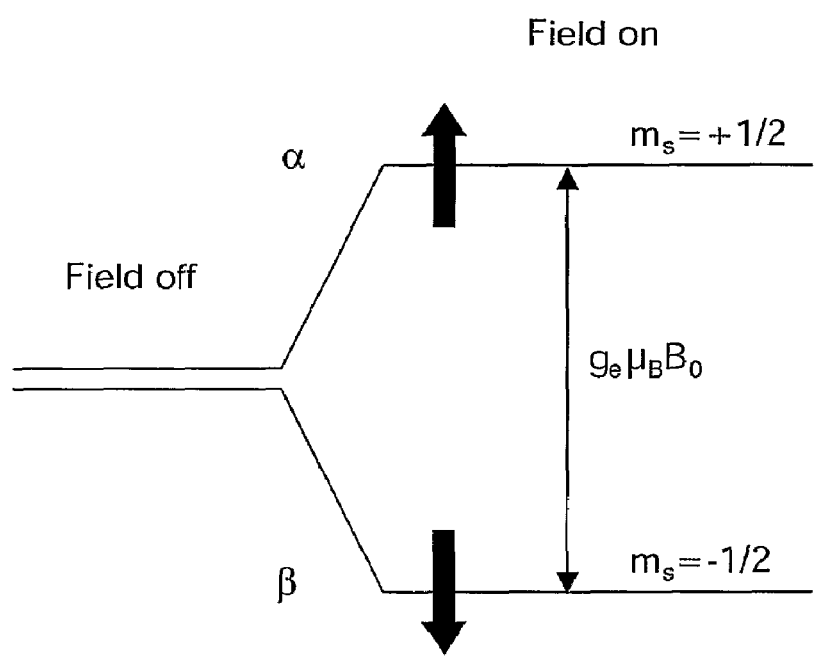
FIG. 2 is an illustration of the Zeeman effect in case of EPR.

In the different figures, the same reference figures refer to the same or analogous elements.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The present invention provides a method and device 1 for on-chip magnetic resonance measurements. The invention will be described by means of a device for on-chip magnetic resonance spectroscopy, but the invention is not limited hereto. The present invention may be applied to spectroscopy methods such as e.g. NMR, EPR, ESR, FMR, SPR. The device 1 and method of the present invention may be applied to non-magnetic as well as magnetic materials, and to solids, liquids and gases. In the following description, the device and method according to the present invention will be described with respect to a magneto-resistive sensor. However, the present invention also does apply in case of other magnetic field sensors such as for example Hall sensors, magneto-impedance sensor or magneto-restriction sensors.

Figure 3:
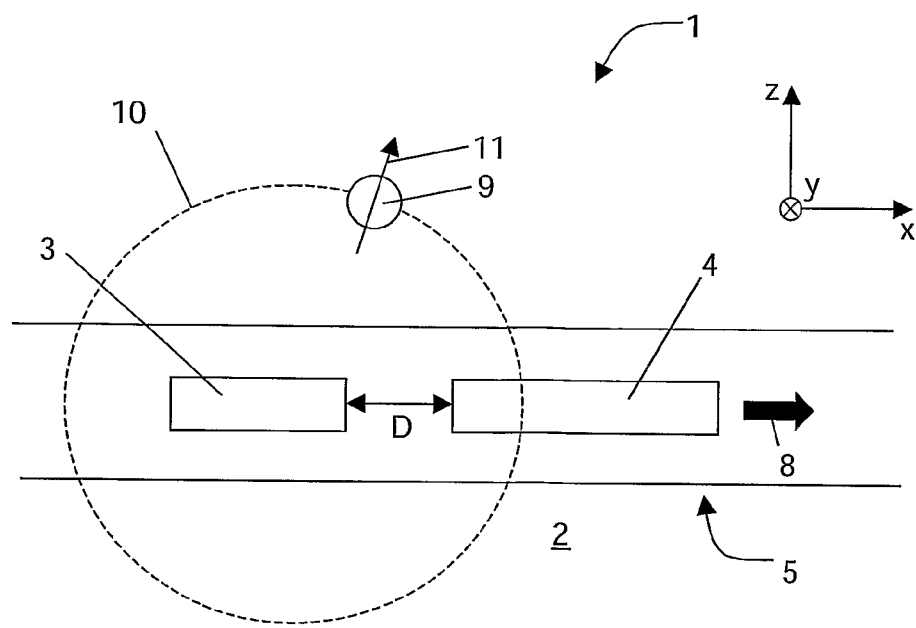
FIG. 3 is a schematic cross-sectional representation of a device according to an embodiment of the present invention.

A device 1 according to an embodiment of the present invention is shown in FIG. 3. The device 1 may comprise a chip that on its turn may comprise a substrate 2, with on a surface thereof at least one conductor 3 and at least one magnetic sensor which in this embodiment is a magneto-resistance sensor 4. In embodiments of the present invention, the term "substrate" may include any underlying material or materials that may be used, or upon which a device, a circuit or an epitaxial layer may be formed. In other alternative embodiments, this "substrate" may include a semiconductor substrate such as e.g. doped silicon, a gallium arsenide (GaAs), a gallium arsenide phosphide (GaAsP), an indium phosphide (InP), a germanium (Ge), or a silicon germanium (SiGe) substrate. The "substrate" may include for example, an insulating layer such as a $SiO_2$ or a $Si_3N_4$ layer in addition to a semiconductor substrate portion. Thus, the term substrate also includes silicon-on-glass, silicon-on sapphire substrates. The term "substrate" is thus used to define generally the elements for layers that underlie a layer or portions of interest. Also, the "substrate" may be any other base on which a layer is formed, for example a glass, a polymer or metal layer.

Figure 4:
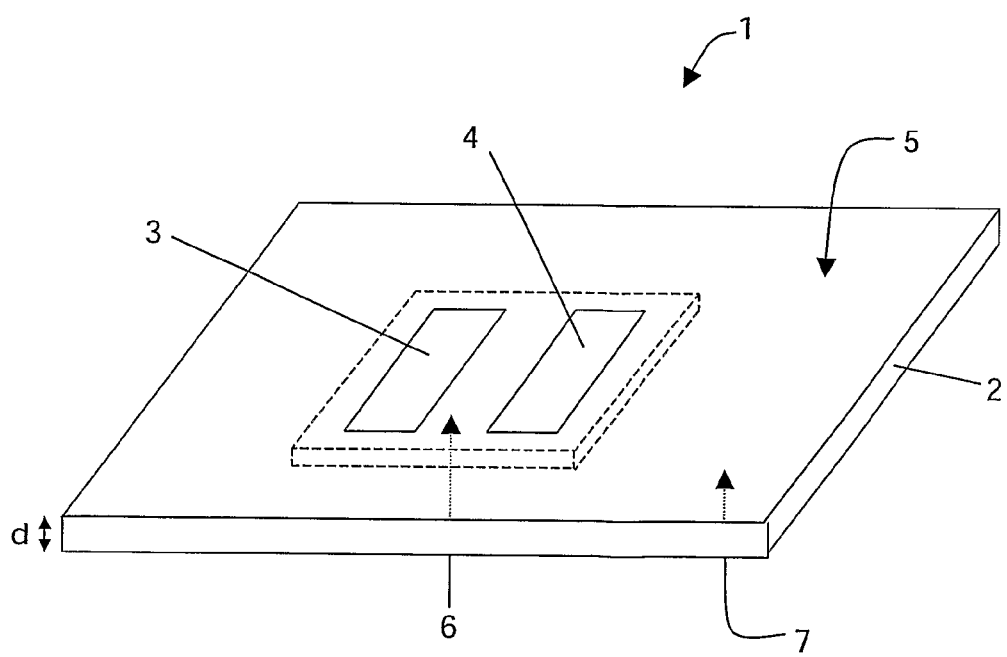
FIG. 4 shows a top view of the device illustrated in FIG. 3.

In one embodiment, the device 1 may comprise a conductor 3 and a magneto-resistance sensor 4, which may be positioned adjacent to each other within a close distance D at a first side 5 of the substrate 2 (FIG. 3 and FIG. 4). For the reason of simplicity the electrical leads connecting to the conductor 3 and the sensor 4 have not been sketched in FIG. 4. The distance D between the magneto-resistance sensor 4 and the conductor 3 is at least a few nanometer, for example 2 nm or more, as an electrical barrier has to be formed between the magneto-resistance sensor 4 and the conductor 3. It has to be noted that the conductor 3 and sensor 4 may also be placed in other ways with respect to each other, e.g. at different depths into the substrate or placed above each other rather than beside each other.

An advantage of a small distance D between the conductor 3 and the sensor 4 is that the excitation current is very close to the spins that need to be excited and detected by the sensor. Hence, a small D gives an energy-efficient architecture, suitable for miniaturisation and integration. The distance D may also be larger, e.g. 10 μm or even up to 1 mm. Larger distances give advantages in ease of manufacturing but give disadvantages in miniaturisation and integration.

The conductor 3, may for example be a current wire, and the magneto-resistance sensor 4 may for example be an AMR, GMR or TMR type sensor. Furthermore, the magneto-resistance sensor 4 may for example have an elongate geometry, e.g. a long and narrow strip geometry, but is not limited to this geometry. Moreover, the magneto-resistance sensor 4 may be of small size. The sensitive region of the sensor 4 may generally be determined by the location where thin-film conducting leads make contact to the sensor material. The length of the magneto-resistance sensor 4 may be between 10 nm and several thousands micrometer, depending on the size of the sensitivity area preferred. The width of the sensor typically is about 3 μm, but can be downscaled to 10 nm. The minimum length and width may partly be determined by the effect of magnetic shape anisotropy, which becomes important when the length and/or width of the sensor 4 are reduced. The thickness of the sensor 4 typically is in the order of 50 nm, but may for example have other values, e.g. between 1 nm and 100 micrometer.

Figure 5:
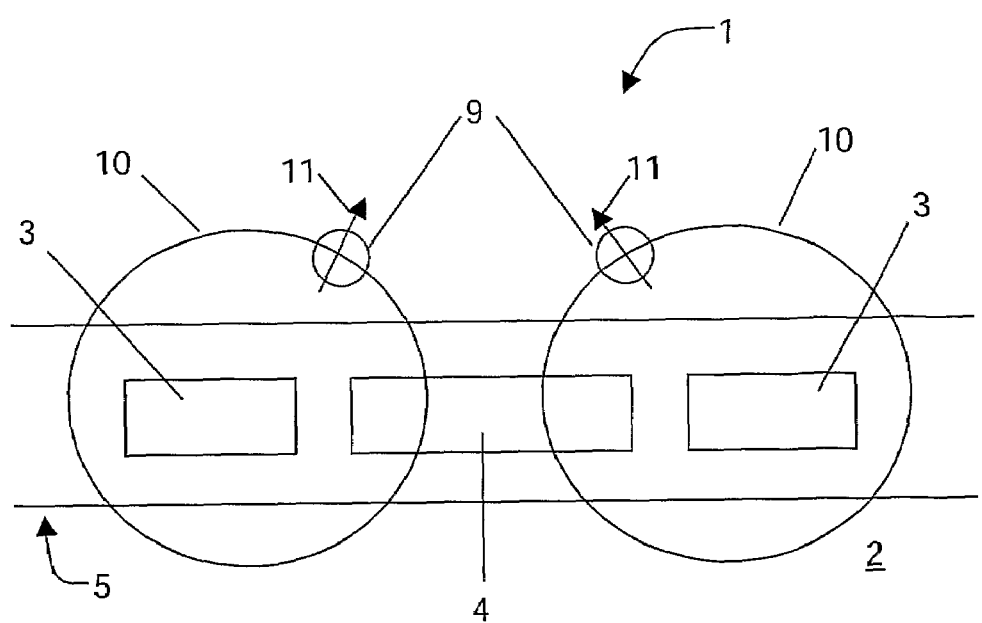
FIG. 5 is a schematic representation of a device according to another embodiment of the present invention.

In another embodiment, the device 1 may comprise a first and a second conductor 3 and a magneto-resistance sensor 4, wherein each conductor 3 may be positioned adjacent an opposite side of the magneto-resistance sensor 4 at a same position with respect to the plane of the magneto-resistance sensor 4 (FIG. 5). The use of more than one conductor 3 and control of the currents therein allows a flexible control of the magnetic fields in the vicinity of the sensor 4. For example, when the currents in the conductors 3 are similar of magnitude and direction, the magnetic fields between the conductors 3 in the vicinity of the sensor 4 are essentially oriented in-plane. Or when the currents in the conductors 3 are of similar magnitude but of opposite direction, the fields between the conductors 3 in the vicinity of the sensor 4 are oriented essentially out-of-plane.

In a further embodiment, conductors 3 and magneto-resistance sensors 4 are positioned alternatingly in an area which needs to be made sensitive for measuring materials, e.g. magnetic particles. The distances between the magneto-resistance sensors 4 and the conductors 3 may very between 2 nm and 5 μm, but may also go up to several millimeters.

Furthermore, in some embodiments according to the present invention, to the device 1 of the present invention an external magnetic field generator 6 (FIG. 4) is provided which may for example be a permanent magnet or an electromagnet, e.g. a coil and an source of electrical energy. The magnetic field generator 6 may be positioned close to the chip such as for example at a second side 7 of the substrate 2, the second side 7 being positioned opposite to the first side 5 of the substrate 2, at which the conductor 3 and the magneto-resistance sensor 4 are positioned. The magnetic field generator may be integrated with the chip or the chip may be mounted on the field generator or the field generator may be a separate device.

The external magnetic field generator 6 generates a magnetic field, which in the present invention acts as a spin orienting magnetic field with respect to the material to be analysed. The orientation of the field can be in-plane as well as out-of-plane. Currents in conductor 3 can also contribute to the orienting field.

In the following, the principle of operation of an embodiment of on-chip magnetic resonance is described. In FIG. 3 a co-ordinate system is introduced to indicate that if the device 1 is positioned in the xy plane, the magneto-resistance sensor 4 mainly detects e.g. the x-component of a magnetic field, i.e. the x-direction is the sensitive direction of the magneto-resistance sensor 4. Arrow 8 in FIG. 3 indicates the sensitive x-direction of the magneto-resistance sensor 4 according to the present invention. The magneto-resistance sensor 4 has a minimum sensitivity in the direction perpendicular to the plane of the device 1, i.e. the z-direction or the vertical direction in FIG. 3. When a high orienting field is desired, it should preferably be oriented along the z-axis, so as to avoid large signals in the field sensor 4 and so as to avoid saturation of the field sensor 4. An external field that is oriented out-of-plane can be relatively high while hardly being detected by the magneto-resistance sensor 4 in absence of a sample 9 that has to be analysed. When a sample 9 that has to be analysed is in the neighbourhood of the device 1, applying an external magnetic field will lead to the sample spins 11 orienting along the direction of the external magnetic field. These spins can either be of nuclear or electronic origin or may be a coupled system of electron spins, i.e. in the case of the detection of ferromagnetic or superparamagnetic materials.

If a current is sent through the conductor 3, it generates in-plane electromagnetic field components 10 at the location of the sample 9. If this is performed at the correct time and/or frequency and/or in the right pulse sequence, this excites the precession of the spins 11 in the sample 9, leading to an in-plane field components at the location of the magneto-resistance sensor 4. In that way, the time-dependent orientation and relaxation of the magnetic moment of the sample spin 11 may be measured by the magneto-resistance sensor 4 and may be recorded as a function of time or frequency. This allows to obtain a magnetic resonance spectrum, e.g. an NMR, EPR, FMR or SPR spectrum. A convenient way to measure the resonance spectrum is by varying the applied magnetic field while keeping the frequency of the AC perturbation field fixed. The period of the AC perturbation field is selected to be larger than the minimum response time of the magnetic sensor 4 (the minimum response time of a GMR sensor is often in the range of 0.1-1 ns).

EPR is based on the resonance of electronic spins, with moments of the order of $g.\mu_B = 1.9 \times 10^{-23}$ A.m$^2$. In an orienting field of 1 T the resonance frequency of a single free electron spin is 28 GHz/T.

In large instruments EPR is typically detected at constant frequency in a sweeping orienting magnetic field. The reason for that is that it is relatively difficult to change the RF frequency in the resonators that are used. However, in the device 1 of the present invention detection may be performed by either sweeping the orienting magnetic field using on-chip means to generate a magnetic field or an additional external magnetic field generator (not represented in the drawings), or by changing the RF frequency. The latter is performed by varying the AC frequency of the current in the conductor.

An embodiment of the present invention aims for orienting magnetic fields of moderate or low magnitude, e.g. 0.001-1 T, that may be generated by a small external magnetic field generator 6 at room temperature and/or current wires on the chip itself.

To achieve distinguishable lines in the measured spectrum, the spin-orienting magnetic field needs to be sufficiently uniform above the magneto-resistance sensor 4. Note that the uniformity requirement strongly depends on the type of measurement (e.g. NMR, FMR) as well as on the material that is to be analysed. The uniformity requirement applies to the sensitivity volume of the device 1. When for example it is assumed that the magneto-resistance sensor 4 has a surface area of 6×100 μm², and that the sensitivity-depth of the magnetic sensor is small (e.g. 1 micrometer), then the magnetic field needs to be uniform in the sensitivity volume of 6 μm×100 μm×1 μm. The orienting magnetic field may be generated by external as well as by on-chip field generators. Due to miniaturisation of the device 1, it is rather easy to achieve a sufficiently high field uniformity. It has to be noted, however, that the magnetic material of the field sensor 4 may somewhat perturb the orienting field and generate some field non-uniformity. Therefore, in an embodiment of the present invention, at least one additional external magnetic field generator (e.g. added magnetic material and/or current conductors, not represented in the drawings) may be placed on or near the chip to reduce the field non-uniformity.

If in one embodiment of the present invention the magneto-resistance sensor 4 is, for example, a GMR sensor with resistance R and linear sensitivity $S_{GMR}$, then the sensitivity of on-chip magnetic resonance may be determined as follows.

The voltage signal of the GMR sensor is given by Eq. 4:

$$V = I \cdot S_{GMR} \cdot H_x \quad \text{(Eq. 3)}$$

with I the sense current through the GMR sensor 4, $S_{GMR}$ the sensitivity of the GMR sensor 4, and $H_x$ the in-plane field resulting from the oriented spins 11. The minimum detectable voltage may be determined by the thermal noise of the sensor 4, as given by Eq. 5:

$$V_{th} = \sqrt{4k_b TRB} \quad \text{(Eq. 4)}$$

with T the temperature, R the resistance of the sensor 4, and B the bandwidth (i.e. the inverse integration time). Typically, the resistance R may be of the order of for example 1 kΩ and B may for example be about 1 Hz. Hence, the minimum detectable voltage in this case equals $V_{th}$~4 nV (T=298 K, R=1 kΩ).

The in-plane field generated by a uniform surface spin density n above the sensor stripe, may approximately be given by Eq. 6 (this is only an order-of-magnitude estimation):

$$H_x \cong \frac{2\varepsilon mn}{\pi w} \quad \text{(Eq. 5)}$$

with ε the fraction of spins 11 contributing to the signal (0<ε<1), m the magnetic moment per spin 11, and w the width of the sensor strip 4.

Combining the above equations, while neglecting non-uniformities and three-dimensional field and magnetization distributions, the detection limit of on-chip resonance in the present invention may be estimated as follows:

$$n \cong \frac{\pi w V_{th}}{2\varepsilon m I S_{GMR}} \quad \text{(Eq. 6)}$$

If for a specific example a GMR strip 4 with w=6 μm, a sensor surface of 6 μm×1000 μm and $S_{GMR}$=0.2 Ωm/A is used and $V_{th}$=4 nV and I=1 mA, then the detection limit is n~$10^{-10}$/(ε.m) for systems that use the above GMR strip as a magneto-resistance sensor 4.

The contributing fraction ε may be determined by the thermal distribution:

$$\varepsilon_{th} = \tanh\left(\frac{2mB}{k_b T}\right) \quad \text{(Eq. 7)}$$

For protons (NMR) $\varepsilon_{th}$=(μ$_p$B)/(k$_b$T)~7×10$^{-6}$ at room temperature (298K), an external magnetic field of B=1 T and with μ$_p$=1.5×1 O$^{-26}$ A.m². Thus the product ε.m (m=μ$_p$ in this case) equals 1×10$^{-31}$ A.m². This corresponds to a surface spin density n=1000 nm.$^{-2}$ (Eq.6), assuming that the detection volume extends about one micrometer. The field at the sensor 4, originating from a spin, decreases as a function of spin-to-sensor distance. As a result, the detection depth depends on the size of the sensor 4. A sensor 4 with a width of for example a micrometer has a detection depth of the order of one micrometer. Into the sample 9, the concentration limit is (1000 nm$^{-2}$/1 μm) which equals to a bulk concentration of 1.6 mol/L (Avogadro constant=6.022×10$^{23}$ mol$^{-1}$). This is a high concentration, getting close to the 100 mol/L for protons in water. Consequently, the sensitivity of the nuclear magnetic resonance technique is rather limited.

For single electrons (in EPR) $\varepsilon_{th}$≈(gμ$_B$B)/(k$_b$T)~5×10$^{-3}$ at a field of 1 T and with gμ$_B$=1.9×10$^{-23}$ A.m², leading to ε.m (m=gμ$_B$ in this case)=9×10$^{-26}$ A.m². EPR may also be performed on multi-spin particles, such as for example, superparamagnetic or ferromagnetic nanoparticles. The particles may have a moment of 10$^{-20}$ A.m² or much higher, e.g. 10$^{-12}$ A.m². Due to the high moment, the particles are nearly completely oriented ($\varepsilon_{th}$~1) in a field of 1 T, giving ε.m=10$^{-20}$ A.m² and higher. In other words, in case of EPR/FMR, the product ε.m ranges from 9×10$^{-26}$ A.m², to 10$^{-20}$ A.m² and higher. Thus n ranges from 10$^3$ μm$^{-2}$ to 0.01 μm² and lower [cf. Eq.(6)]. Again assuming that the detection volume extends about a micrometer into the sample 9 the concentration limit ranges from 1.6 μmol/L (1000 μm$^{-2}$/1 μm) to 16 pmol/L (0.01 μm$^{-2}$/1 μm) and lower. Hence, with on-chip magnetic resonance using EPR/FMR it is possible to analyse samples with low concentrations.

Consequently, although on chip NMR measurements can be performed, the sensitivity may be relatively low. The sensitivity for on chip EPR/FMR measurements may be significantly higher.

Figure 6:
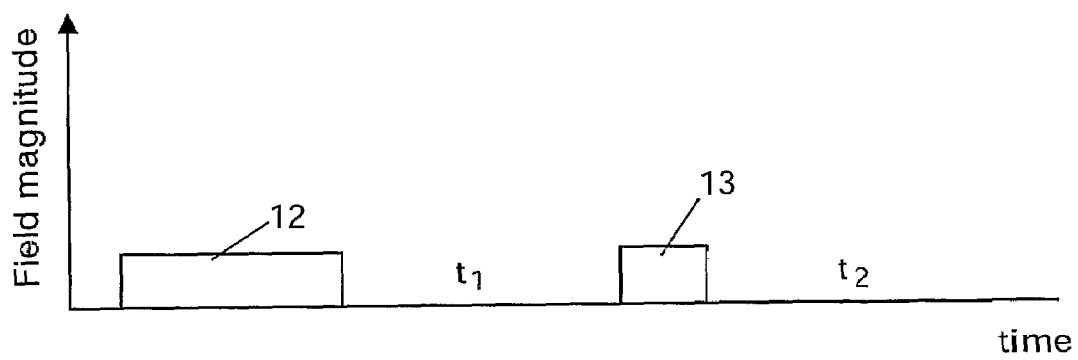
FIG. 6 shows a schematic outline of 2D NMR spectroscopy.

The detection specificity of the method of the present invention may be enhanced by using pulse sequences, as is used in multi-dimensional NMR. As an example, the schematic outline of two-dimensional spectroscopy is shown in FIG. 6. During the preparation pulse or pulse sequence 12 the initial state of the spins 11 is established. After this, a time period t$_1$ follows, which is called the evolution period. During the evolution period each spin 11 will precess with its own frequency. With a pulse, or a series of pulses, magnetisation is transferred between a first and a second spin 11. The period in which this happens is called mixing period 13. After this mixing period 13, a detection period t$_2$ completes the experiment. During the detection period, the magnetisation of the second spin 11 will precess with the Larmor frequency (i.e. the frequency of precession) of this spin 11. The measured signal becomes dependent upon two time variables: the time during which the signal is measured ($t_2$) and the so-called indirect dimension variable $t_1$.

The resonance spectrum has narrow characteristic peaks (e.g. NMR peak widths may be as narrow as for example 1-2 Hz) which point to the material type and material properties. Magneto-resistance sensors 4 are highly sensitive to fields generated by magnetic moments in the vicinity of the sensor 4. Therefore, the method of the present invention is suitable for miniaturised materials analysis such as for example microfluidics and may be integrated in for example silicon technology.

The technology of the present invention may be the basis of high performance disposable products. Each product may contain for example a sub-mm² silicon die. The die may be packaged in plastic to form a disposable diagnostic cartridge for e.g. the analysis of fluids or gases that are inserted into the cartridge. Also, the die may be package in a plastic read-head, which analyses material that is brought in the vicinity of the read-head. The strength of the method of the present invention lies in the combination of highly efficient magnetic field near on-chip conductors 3 with very sensitive on-chip magneto-resistance sensors 4.

The device 1 and method of this invention may be used for materials analysis in consumer as well as professional applications such as for example personal care (skin analysis), food diagnostics, biomedical diagnostics, identification and authentication, environmental monitoring, mobile applications, . . . . The device 1 may also be suitable to analyse or detect paramagnetic elements or molecules such as for example paramagnetic oxygen, NO or Fe.

Another application of the device 1 and method of the present invention is materials fingerprinting, e.g. clinical blood fingerprinting. Presently, blood fingerprinting is being developed with mass-spectrometry. It relies on the extraction of a group of interesting molecules from blood using an adsorptive substrate and subsequent label-free analysis by mass spectrometry. The blood fingerprinting application requires that the spectroscopic technique operates on a very small amount of material. The device 1 of the present invention aims at the analysis of small amounts of material and therefore it may allow blood fingerprint applications.

Biomedical tests often employ detection labels. In the device 1 of the present invention magnetic labels, e.g. magnetic molecular labels or magnetic particle labels, may be used for labelled (e.g. sandwich assay) or unlabelled detection (e.g. in a displacement assay, or in an assay using spin-labels which change resonance properties upon interaction with biological species).

Furthermore, the spectroscopic method of the present invention may be applied to non-magnetic as well as magnetic materials, and to solids, liquids and gases. Different magnetic labels may be identified by their resonance spectrum, enabling label identification or so-called bar-coding. This may help to distinguish first and second beads in two-bead magnetic stringency. Furthermore, bar-coding may help to distinguish different labels or beads, and thereby reduce non-specific signals when labels or beads bind on other-than-the-intended spots on a biochip. The use of different detectable magnetic labels is also useful in molecular diagnostics, because it facilitates detection of different molecules. Often different types of labels are combined in an assay, to allow for example the use of concurrent controls, for comparative binding/hybridisation assays, and to reduce non-specific cross-signals in a multiplexed sandwich assay. We refer to the use of separately detectable labels as 'label multiplexing'. In the further description, for the ease and simplicity of writing and understanding only, magnetic molecular labels or magnetic particles will be referred to as particles.

In a further embodiment, device 1 allows the detection of separately detectable labels, i.e. it allows the use of label multiplexing.

The magnetic particles used for label multiplexing typically have a diameter between 3 nm and 5 µm and contain one or more magnetic cores. The diameter of the core(s) typically is between 0.5 nm and 100 nm. The particles may typically be coated by a protective shell, e.g. ligands and/or an organic or polymer material such as polystyrene or dextrane and/or a metallic coating such as gold. The particles may have a saturation magnetic moment typically of the order of $10^{-23}$–$10^{-12}$ A.m². The use of magnetic particles allows to perform ferromagnetic or superparamagnetic resonance spectroscopy, whereby magnetic resonance is measured in a material with coupled spins. The important advantage of magnetic nanoparticles is that these have a large total moment, giving already strong alignment in a practically realizable external magnetic field. In this case, the $\epsilon_{th}$~1 in eq.7. Thus, FMR and SPR have a high sensitivity and therefore allow a good signal to noise ratio, which is necessary if differences in the magnetic characteristics of multiplexed labels need to be measured. The FMR and SPR resonance frequency for magnetic particles is essentially the same as for EPR. In addition to influences of the external field, the resonance frequency also depends on the magnetic anisotropy, e.g. crystal anisotropy and shape anisotropy. Stated differently, the FMR resonance frequency is a function not only of the externally applied field but also of the internal field due to the magnetic anisotropy of the magnetic particles:

$$f=f(B_{ext}, K) \tag{Eq.8}$$

Thus, as the resonance frequency is not only a function of the external field applied to the magnetic particle, but also depends on the internal field created due to the magnetic anisotropy of the particle, it is possible to distinguish magnetic particles according to their internal magnetic field. For label multiplexing, which can e.g. be used in a bio-molecular test, labels having different magnetic properties are necessary. Several ways exist to produce magnetic particles with different magnetic properties, e.g. due to different chemical composition, different size, different shape, different crystallinity, different chemical additives, different surface treatment, etc. In some cases the particles can contain the same chemical elements but differ in structure due to a different treatment during manufacturing, e.g. different annealing steps.

At least the following types of magnetic beads can be used as detection labels, in particular for label-multiplexing:

A first type of beads has different saturation fields, for example given by using cores with different sizes. In this case the magnetic signal is measured as a function of applied field.

A second type of beads has cores of different magnetic anisotropy. The magnetic anisotropy depends on the core crystallinity, the materials composition of the cores and the core shape. The anisotropy causes a different magnetisation relaxation time and a different resonance frequency, which allows to detect these particles. Measurement of relaxation time can be performed by applying field pulses and recording the signal as a function of time. Magnetic particles having a different magnetic anisotropy can e.g. be made by applying different annealing treatments to materials such as FePt. Depending on the annealing temperature, the particles either are a random substitutional FePt allow with low coercive field and low anisotropy or are an ordered FePt compound with a high coercive field and high uniaxial crystal anisotropy. The annealing conditions thus can be used to tune the magnetic anisotropy and thus allows multiplexing. Other possible post-treatments to change magnetic properties may for example be ion bombardment, chemical treatment (e.g. etching), etc.

A third type of beads may have different properties as a function of temperature, given by using materials of which the crystal anisotropy depends sensitively on the temperature. Small temperature changes around room temperature (e.g ±10 K) can give large changes of crystal anisotropy, which is easily detected. Heating can for example be done in a pulsed way by a resistor on the chip.

A fourth type of particles may comprise materials with different damping of magnetic resonance. The damping is caused by energy dissipation to the environment, e.g. due to surface roughness of the particle in the case of FMR or SPR.

For bio-molecular or (bio)chemical diagnostics, the magnetic particles are used as labels and can be specifically connected to other molecules, for which e.g. the concentration needs to be measured using capturing or targeting molecules. These can be nucleic acids, proteins, saccharides, etc. Also other biological materials may be targeted, such as for example cells, cell fragments, tissue or parts thereof.

When magnetic particles are used as labels, the binding or unbinding of these in the vicinity of the magnetic sensor 4 is detected. Magnetic particles as well as sensor surfaces can be provided with specific capture molecules. For example, if the magnetic particles pass the biosensor they can be bound to the sensitive surface, depending on the presence or absence of a target molecule.

Using device 1, the magnetic resonance properties of the collection of particles can be measured. The anisotropy axes of the particles can be oriented in a magnetic field, which avoids magnetic-resonance peak broadening due to very different alignments. The rotational alignment is possible due to the fact that the particles are embedded in a viscoelastic medium, e.g. an open organic layer on the surface of the biosensor. It has to be noted that particles may be detected on and/or near the sensor 4 surface. Particles as well as clusters of particles may be detected and distinguished due to their different magnetic-resonance characteristics, which may be relevant for example cluster assays.

Besides the resonance frequency, the particles can be identified according to the measured FMR damping. The damping is caused by energy dissipation to the environment, e.g. due to surface roughness of the particle.

Furthermore it is a specific advantage of FMR that the frequency can be tuned for maximum signal-to-noise ratio, for example by selecting the frequency to be above the high-noise regime of the magnetic sensor, i.e. above the 1/f noise band, typically f>10 kHz for example GMR sensors.

Magnetic detection techniques furthermore have advantages over optical techniques, as they allow a low background, the possibility to actuate labels for stringency and the possibility for target extraction.

Another advantage of the device and method according to the present invention is that it may allow an improved signal-over-background ratio, where background refers to unwanted signals due to naturally occurring sample components with magnetic activity or due to sample contamination involving magnetic activity or due to sample contamination involving magnetic activity. An improved signal-over-background is particularly important when measurements are performed in complex and strongly variable materials, such as for example complex biological or chemical mixtures. An improved signal-over-background may improve the sensitivity and specificity of the assay, enhance the precision and reliability of the assay, reduce the number and/or complexity of assay steps and enhance the speed of the total assay.

It is to be understood that although preferred embodiments, specific constructions and configurations, as well as materials, have been discussed herein for devices according to the present invention, various changes or modifications in form and detail may be made without departing from the scope and spirit of this invention.

The invention claimed is:

1. A device for on-chip magnetic resonance measurements for use with a first orienting magnetic field, the device comprising a chip, said chip comprising,
    on-chip means for creating a second electromagnetic field to excite precession of oriented spin magnetic moments in a sample to be analyzed, and
    at least one magneto-resistance sensor for on-chip detection of a magnetic precession of the spin magnetic moments about the first orienting magnetic field in the sample to be analyzed.

2. The device according to claim 1, the chip lying in a plane, wherein said on-chip means for creating a second electromagnetic field and said magnetic sensor are positioned adjacent each other in the plane of the chip.

3. The device according to claim 1, the chip lying in a plane, wherein the means for creating a second electromagnetic field comprises a conductor adjacent the magnetic sensor.

4. The device according to claim 1, the chip lying in a plane, wherein the means for creating a second electromagnetic field comprises two conductors, each of the conductors being positioned adjacent one of two opposite sides of the magnetic sensor at a same position with respect to the plane of the chip.

5. The device according to claim 1, further comprising a first orienting magnetic field generator external to the chip.

6. The device according claim 5, wherein said first orienting magnetic field generator is a permanent magnet.

7. The device according to claim 5, wherein said first orienting magnetic field generator is an electromagnet.

8. The device according to claim 5, wherein the first orienting magnetic field generator comprises means to vary a magnetic field strength.

9. The device according to claim 1, wherein said chip furthermore comprises an on-chip first orienting magnetic field generator.

10. The device according to claim 9, wherein said chip has two major surfaces opposite each other, the means for creating a second electromagnetic field and the magnetic sensor being located on a first major surface and the on-chip first orienting magnetic field generator being positioned on the second major surface.

11. The device according claim 1, wherein said magneto-resistance sensor is a GMR sensor.

12. The device according to claim 1, wherein said magneto-resistance sensor is a TMR sensor.

13. The device according to claim 1, wherein said magneto-resistance sensor has an elongated strip geometry.

14. The device according to claim 1, wherein said spin magnetic moments are nuclear spin magnetic moments.

15. The device according to claim 1, wherein said spin magnetic moments are electron spin magnetic moments.

16. The device according to claim 1, wherein said spin magnetic moments are coupled-spin magnetic moments.

17. Use of the device as recited in claim 1, for biological sample analysis or chemical sample analysis.

18. A method for performing on-chip magnetic resonance measurements, the method comprising:

orienting spin magnetic moments inside a sample in a first orienting magnetic field, exciting precession of said spin magnetic moments inside said sample to be analysed, and on-chip detecting of spin magnetic moments precession with a magneto-resistance sensor; and providing an output representative of the detected spin magnetic moments precession for analysis.

19. The method according to claim 18, whereby generating the spin magnetic moments in the first magnetic field, is performed by the first magnetic field being generated external to the chip.

20. The method according to claim 18, whereby generating the first orienting magnetic field is performed by a magnetic field generator integral with the chip.

21. The method according to claim 18, whereby exciting precession of spins inside a sample to be analyzed is performed by generating a second magnetic field.

22. The method according to claim 18, whereby exciting precession of spins inside a sample to be analyzed is performed by sweeping the second magnetic field over at least one of the following: a frequency range, an amplitude range.

23. The method according to claim 18, furthermore comprising sweeping the first orienting magnetic field over at least one of the following: a frequency range, an amplitude range.

24. The method according to claim 18, whereby said sample comprises different types of magnetic particles or molecules.

25. A method according to claim 24, whereby said on-chip detecting of spin magnetic moments precession comprises detecting separate signals originating from different types of magnetic particles or molecules.

* * * * *